United States Patent
Deerin

(10) Patent No.: US 8,123,735 B2
(45) Date of Patent: Feb. 28, 2012

(54) ABSORBENT GARMENT

(76) Inventor: Robert F. Deerin, Durham, NC (US)

( * ) Notice: Subject to any disclaimer, the term of this patent is extended or adjusted under 35 U.S.C. 154(b) by 259 days.

(21) Appl. No.: 12/373,666

(22) PCT Filed: Jul. 10, 2007

(86) PCT No.: PCT/US2007/073100
§ 371 (c)(1),
(2), (4) Date: Apr. 24, 2009

(87) PCT Pub. No.: WO2008/008743
PCT Pub. Date: Jan. 17, 2008

(65) Prior Publication Data
US 2009/0299311 A1    Dec. 3, 2009

(51) Int. Cl.
*A61F 13/15* (2006.01)
(52) U.S. Cl. ............... 604/396; 604/385.14; 604/385.15
(58) Field of Classification Search ............... 604/396, 604/385.14, 385.15
See application file for complete search history.

(56) References Cited

U.S. PATENT DOCUMENTS

| | | | |
|---|---|---|---|
| 3,489,149 A | | 1/1970 | Larson |
| 3,613,686 A | | 10/1971 | De Woskin |
| 4,352,356 A | | 10/1982 | Tong |
| 4,813,950 A | | 3/1989 | Branch |
| 5,098,419 A | | 3/1992 | Gold |
| 5,267,991 A | | 12/1993 | Gillies et al. |
| 6,041,446 A | * | 3/2000 | Braunstein et al. ............... 2/400 |
| 6,110,479 A | * | 8/2000 | Blaney et al. ............... 424/402 |
| 6,240,569 B1 | | 6/2001 | Van Gompel et al. |
| 6,393,621 B1 | | 5/2002 | Redwine et al. |
| 6,605,071 B1 | * | 8/2003 | Gray et al. ............... 604/385.28 |
| 2005/0228356 A1 | | 10/2005 | LaVon et al. |

FOREIGN PATENT DOCUMENTS

CA 2365577 A1 6/2003
WO 02067833 A1 9/2002

OTHER PUBLICATIONS

Incontinence Briefs, Carol Wright Gifts, Item Nos. 57943, 52043, and 57968, http://www.carolwrightgifts.com/Personal-Care/Health-Products/Incontinence-Briefs/57943.cfm.
Wearever Incontinence Lace Briefs, ASIN: B000086501, sold by Lady Grace, http://www.amazon.com/Wearever-Incontinence-Lace-Brief/dp/B00008650I/ref=sr_11_1?ie=UTF8&qid=1240405921&sr=11-1.
Reusable Incontinence Brief, ASIN: B00022AJRK, sold by National, http://www.amazon.com/Reusable-Incontinence-Brief-Beige-Small/dp/B0002KQXR2/ref=sr_11_1?ie=UTF8&qid=1240406035&sr=11-1.

(Continued)

*Primary Examiner* — Jacqueline F. Stephens
(74) *Attorney, Agent, or Firm* — Matthew W. Witsil; Moore & Van Allen PLLC

(57) ABSTRACT

A washable, reusable garment for retention of body fluids when worn on a person's lower body part. The garment has a crotch portion and a body portion. The crotch portion has an absorbent composite, and a pocket adapted for receiving a removable absorbent pad. The body portion has a waist opening and is seamless except where attached to the crotch portion. The body portion and the crotch portion together form first and second leg openings.

34 Claims, 2 Drawing Sheets

OTHER PUBLICATIONS

Robert F. Deerin, PCT Notification Concerning Transmittal of International Preliminary Report on Patentability, issued in corresponding International Patent Application No. PCT/US2007/073100, Jan. 22, 2009.

Robert F. Deerin, PCT Written Opinion, issued in corresponding International Patent Application No. PCT/US2007/073100, Jan. 22, 2009.

* cited by examiner

ABSORBENT GARMENT

TECHNICAL FIELD

The present invention is directed to an absorbent garment or panty for the absorption and retention of a liquid, and more particularly, a washable, reusable garment.

BACKGROUND

Various garments, having a pant-like configuration and being useful as incontinence garments, menstrual garments, training garments, diapers, and the like, are commercially available, as well as being disclosed in various patents.

For instance, machine washable, and thus reusable, incontinence briefs having seams, and having an absorbent HYDREX™ pad sewn into the crotch area can be purchased from the Carol Wright Gifts catalog under item nos. 57943, 57968, and 52043, or from www.amazon.com under item no. B000086501 (sold by Lady Grace) or under item no. B0002KQXR2 (sold by National). Additionally of background interest is U.S. Pat. No. 6,240,569 to Van Gompel, et al., which discloses a disposable (not machine washable) panty having an absorbent barrier composite pad positioned in the crotch area.

Also of interest is U.S. Pat. No. 3,489,149 to Larson, which discloses a menstrual panty having a pocket sewn into the crotch area, the pocket being for receiving an absorbent disposable menstrual pad. Similarly, U.S. Pat. No. 4,352,356 to Tong discloses a urinary incontinence panty having a pouch connected in the crotch area and adapted to receive an absorbent disposable urinary incontinence pad. Another sanitary panty garment with a pocket in the crotch area is disclosed in U.S. Pat. No. 3,613,686 to Woskin.

The crotch area of a menstrual or incontinence garment may be impregnated, coated or laminated with a barrier film which prevents or retards movement of liquid out of the garment and onto the wearer's legs. For instance, U.S. Pat. No. 5,098,419 to Gold shows an undergarment to be worn by an incontinent person, the garment having a modified polyester-polyurethane impregnated into the crotch portion of the garment. Also, the above-noted U.S. Pat. No. 6,240,569 to Van Gompel, et al. shows that adjacent the absorbent barrier composite pad is a barrier film, which is a microporous film produced by Mitsui and sold by consolidated Thermoplastics under the trademark ESPOIR® N-TAF-CT. Similarly, U.S. Pat. No. 4,813,950 to Branch shows the crotch area of a sanitary menses panty lined with a non-woven barrier film that permits the passage of gases such as water vapor but prevents the passage of liquids such as blood and urine, and which is a polyurethane, microporous film sold under the trademark TENDERCARE® by Spenco Medical or under the trademark DUREFLEX® by Deerfield Urethane, Inc. Of background interest is a reusable, washable diaper pad disclosed in U.S. Pat. No. 5,267,991 to Gilles, et al.; the diaper pad has a liquid-absorbent, stitch-bonded layer, sold by Cortaulds Limited under the trade name GALAXY™, and has an outer layer of waterproof polyurethane barrier film that is bonded to the stitch-bonded layer.

Also of interest is U.S. Pat. No. 6,393,621 to Redwine, et al. This patent discloses an undergarment useful with an absorbent article, particularly a menstrual pad of the type that has an adhesive layer covered with a peel off strip that is removed so that the pad can be adhered to the crotch area of the garment. The garment is free of side, front, and back seams, and has improved construction over previous such seamless garments in order to provide a snug fit about the wearer.

The disclosures of all patents, which are mentioned here, are incorporated here by reference.

SUMMARY OF INVENTION

The present invention provides a washable, reusable garment for retention of body fluids when worn on a person's lower body part, the garment comprising: (a) a crotch portion having an absorbent composite, and having a pocket adapted for receiving a removable absorbent pad in a space defined by the pocket, and (b) a body portion having a waist opening and being seamless except where attached to the crotch portion, the body portion and the crotch portion together forming first and second leg openings.

Furthermore, the present invention provides a washable, reusable garment for retention of body fluids when worn on a person's lower body part, the garment comprising: (a) a crotch portion having a pocket, wherein the pocket has a closed end and has an open end adapted for receiving a removable absorbent pad in a space defined by the pocket, (b) an absorbent composite incorporated on one side thereof in the pocket and having a barrier film disposed on another side thereof, inside the space defined by the pocket, and (c) a body portion having a waist opening and being seamless except where attached to the crotch portion, wherein the body portion and the crotch portion together form first and second leg openings, and the body portion is one or both of elastic or stretchable so as to provide a snug fit about the wearer's lower body part.

Also, the present invention provides in combination: (i) a washable, reusable garment for retention of body fluids when worn on a person's lower body part, the garment comprising: (a) a crotch portion having an absorbent composite, and having a pocket adapted for receiving a removable absorbent pad in a space defined by the pocket, and (b) a body portion having a waist opening and being seamless except where attached to the crotch portion, the body portion and the crotch portion together forming first and second leg openings; and (ii) at least one absorbent pad for insertion into the pocket.

Moreover, the present invention provides in combination: (i) a washable, reusable garment for retention of body fluids when worn on a person's lower body part, the garment comprising: (a) a crotch portion having a pocket, wherein the pocket has a closed end and has an open end adapted for receiving a removable absorbent pad in a space defined by the pocket, (b) an absorbent composite incorporated on one side thereof in the pocket and having a barrier film disposed on another side thereof, inside the space defined by the pocket, and (c) a body portion having a waist opening and being seamless except where attached to the crotch portion, wherein the body portion and the crotch portion together form first and second leg openings, and the body portion is one or both of elastic or stretchable so as to provide a snug fit about the wearer's lower body part; and (ii) at least one absorbent pad for insertion into the pocket.

The invention is now discussed in connection with the accompanying Figures as best described below.

DESCRIPTION

Figure 1:
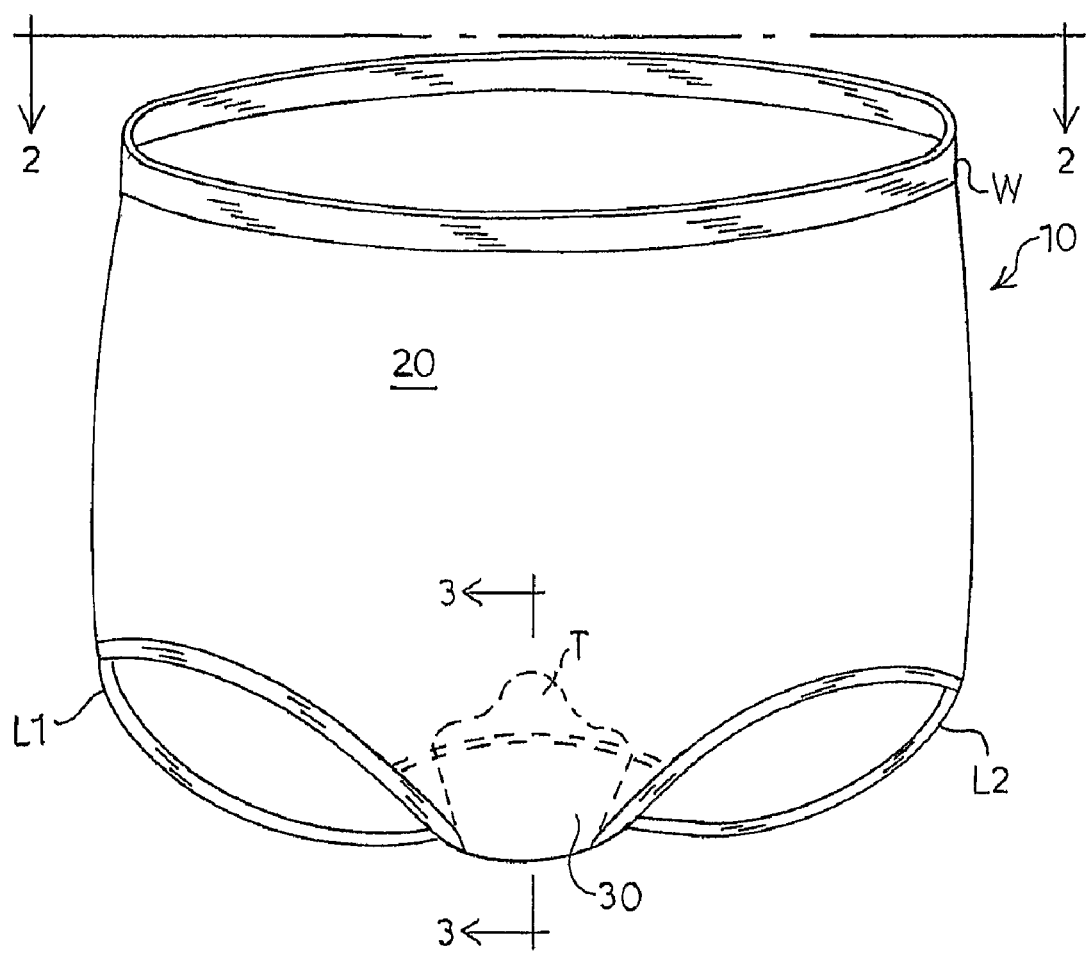
FIG. 1 depicts a front view of an embodiment in accordance with the present invention of a washable, reusable garment for retention of body fluids when worn on a person's lower body part.

As used here, certain terminology is for convenience only and is not to be taken as a limitation on the invention. For instance, words such as "upper," "lower," "left," "right," "top," "bottom," "side," "horizontal," "vertical," "back," "front," "upward," and "downward" merely describe the configuration shown in the Figures. It is understood that the components may be in any direction and the terminology, therefore, should be understood as encompassing such variations unless specified otherwise.

The terms "elastic" and "stretchable" include any material which can be stretched, and which tends to return to its original shape when relaxed.

By the term "seamless" is meant that the body portion of the garment is free of seams in the back, the front, and the sides.

By the term "barrier film" is meant a film that prevents or retards movement of liquid, such as blood and/or urine.

With reference now to the Figures, whenever possible, the same reference numerals and letters are used throughout to refer to the same or like parts.

More specifically, shown in FIG. 1 is a front view of a washable, reusable garment 10 for retention of body fluids when worn on a person's lower body part. The garment 10 is useful as an incontinence garment, a menstrual garment, a training garment, a diaper, and the like.

The garment 10 may be constructed of various materials that are woven, non-woven, or combinations thereof, and may optionally include a moisture wicking agent. Cotton, nylon, and/or polyester, and/or blends thereof are suitable materials. Nylon is a particularly suitable material. Also polyester is a particularly suitable material, and more particularly suitable is an interior top cloth of polyester to which a moisture wicking agent has been applied, such as in a dye bath. Various such moisture wicking agents are known in the art. It is also desirable that the garment 10 should be appropriately elastic and/or stretchable so as to provide a snug fit about the wearer's lower body part.

The garment 10 has a body portion 20 and a crotch portion 30. The body portion 20 has a waist opening W, and is seamless. By seamless is meant that the body portion is free of seams in the back, the front, and the sides, such seams being common to undergarments, and often being undesirable as the seams create panty lines that are often visible through the wearer's outer garment, such as slacks. The body portion 20, together with the crotch portion 30, forms the first and second leg openings L1, L2.

Figure 2:
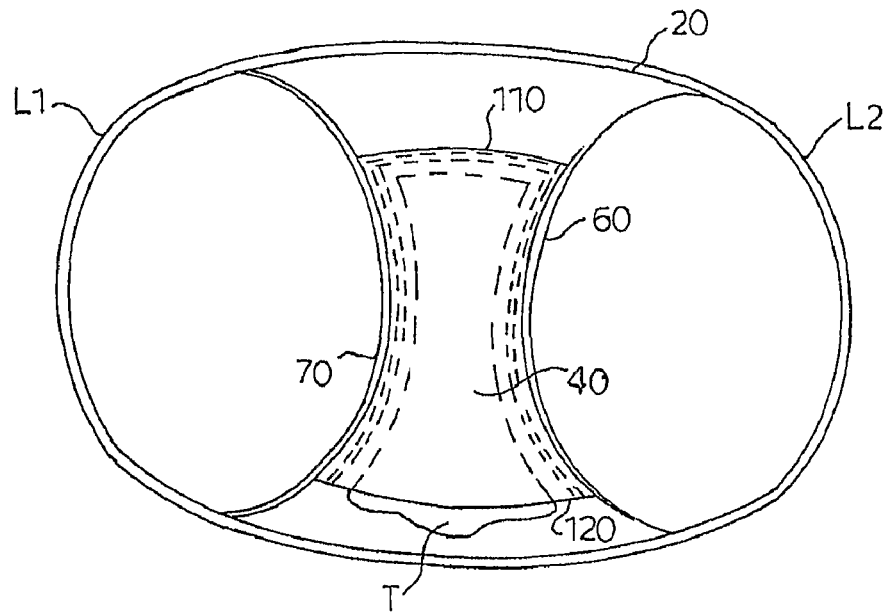
FIG. 2 is a top view, taken in the direction of line 2-2 of FIG. 1, and looking down toward the crotch portion of the garment of FIG. 1.
Figure 3:
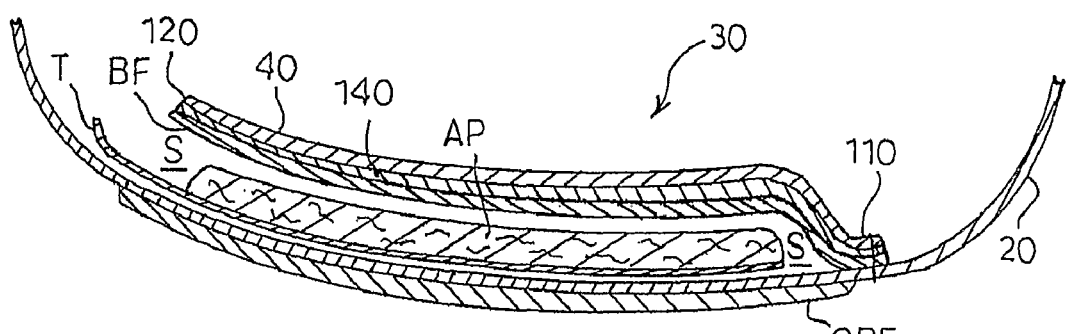
FIG. 3 is a sectional view of the crotch portion of the garment of FIG. 1 taken along line 3-3 of FIG. 1.

FIG. 2 is a top view of the garment 10 taken looking down in the direction line 2-2 of FIG. 1, and toward the crotch portion 30. FIG. 3 is a sectional view of the crotch portion 30 taken along line 3-3 of FIG. 1.

As can be seen, on the inside of the crotch portion 30, there is sewn or otherwise attached a pocket 40, adapted for receiving a removable absorbent pad AP in a space S defined by the pocket 40. The absorbent pad AP may be disposable or reusable, and optionally may be provided with a pull tab T for facilitating removal of the absorbent pad AP from the pocket 40. More particularly, the pocket 40 has two edges 60 and 70, which suitably may be incorporated into the garment 10 at or near the leg openings L1, L2. The back end 110 of the pocket 40 is closed by being sewn or otherwise attached to the garment 10, and the front end 120 of the pocket 40 is left open for receiving the absorbent pad AP.

On the inside of the pocket 40 is included an absorbent composite 140, for absorbing body fluids, such as urine, blood, menstrual flow, et cetera. The absorbent composite 140 may be sewn, or otherwise attached to the pocket 40. The absorbent composite 140 may be constructed of various materials that are woven, non-woven, or combinations thereof, and may be any absorbent material that is suitable for when the garment 10 is washed. One suitable material for the composite 140 is a non-woven fabric of a polyester/rayon blend. One such suitable polyester/rayon blend is commercially available under the trade name, HYDREX™. More preferably, the composite material, such as HYDREX™, contains an antimicrobial agent, such as by the composite material being needle punched with an antimicrobial Agion fiber (from Agion Technologies of Massachusetts). Various such antimicrobial agents for treating the fiber are known in the art, a well known one being silver ion, $Ag^+$. Typically, the antimicrobial agent not only helps obviate infection to the wearer, but also helps obviate odor from the wearer. HYDREX™, needle punched with an Agion fiber having antimicrobial $Ag^+$ is commercially available from Texel, Inc. of Canada.

Preferably, the absorbent composite 140 includes a barrier film BF, which prevents or retards movement of liquid, for instance out of the garment and onto the wearer's legs. Suitably, the absorbent composite 140 may be impregnated, coated or laminated with the barrier film BF, on a side of the absorbent composite 140 inside the space S defined by the pocket 40. Various materials are known as barrier films BF, and particularly suitable for the barrier film BF is polyurethane, and preferably, it is laminated to the barrier composite 140. The term polyurethane is intended to include copolymers thereof that are suitable, such as polyurethane-polyester copolymer. For instance, a urethane film manufactured by Deerfield Urethane, Inc. is very suitable for lamination to the absorbent composite 140, particularly when the absorbent composite 140 is HYDREX™, needle punched with an Agion fiber having antimicrobial $Ag^+$.

Also, an optional barrier film OBF of the same or a different barrier material may be disposed on the outside of the crotch portion 30, such as by lamination.

Although the present invention has been shown and described in detail with regard to only an embodiment of the invention as depicted in the drawings, it should be understood by those skilled in the art that it is not intended to limit the invention to the specific embodiment disclosed. Various modifications, omissions, and additions may be made to the disclosed embodiment without materially departing from the novel teachings and advantages of the invention, particularly in light of the foregoing teachings. Accordingly, it is intended to cover all such modifications, omissions, additions, and equivalents as may be included within the spirit and scope of the invention as defined by the following claims.

What is claimed is:

1. A washable, reusable garment for retention of body fluids when worn on a person's lower body part, the garment comprising: (a) a crotch portion having a washable absorbent composite incorporated in the crotch portion as part of the crotch portion by attachment thereto, and (b) a body portion having a waist opening, the body portion and the crotch portion together forming first and second leg openings, wherein the crotch portion includes a pocket and the washable absorbent composite is incorporated in the pocket.

2. The garment of claim 1, wherein the garment comprises a material chosen from woven, non-woven, or a combination thereof.

3. The garment of claim 2, wherein the material is chosen from cotton, nylon, polyester, or a combination thereof.

4. The garment of claim 2, wherein the material includes a moisture wicking agent.

5. The garment of claim 1, wherein the washable absorbent composite comprises a material chosen from woven, non-woven, or a combination thereof.

6. The garment of claim 5, wherein the washable absorbent composite comprises a non-woven polyester/rayon blend.

7. The garment of claim 1, wherein the washable absorbent composite contains an antimicrobial agent.

8. The garment of claim 7, wherein the antimicrobial agent comprises silver ion.

9. The garment of claim 1, wherein the washable absorbent composite includes a barrier film.

10. The garment of claim 9, wherein the barrier film comprises polyurethane.

11. The garment of claim 9, wherein the barrier film is laminated to the washable absorbent composite.

12. A washable, reusable garment for retention of body fluids when worn on a person's lower body part, the garment comprising: (a) a crotch portion having a washable absorbent composite incorporated in the crotch portion as part of the crotch portion by attachment thereto, and (b) a body portion having a waist opening, the body portion and the crotch portion together forming first and second leg openings, wherein the crotch portion includes on its outside a barrier film.

13. A washable, reusable garment for retention of body fluids when worn on a person's lower body part, the garment comprising: (a) a crotch portion having a washable absorbent composite incorporated in the crotch portion as part of the crotch portion by attachment thereto, and (b) a body portion having a waist opening, the body portion and the crotch portion together forming first and second leg openings, wherein the body portion is one or both of elastic or stretchable so as to provide a snug fit about the wearer's lower body part.

14. A washable, reusable garment for retention of body fluids when worn on a person's lower body part, the garment comprising: (a) a crotch portion having a pocket, wherein the pocket has a closed end and has an open end, (b) a washable absorbent composite incorporated on one side thereof in the pocket as part of the pocket by attachment to the pocket and having a barrier film disposed on another side thereof, inside the space defined by the pocket, and (c) a body portion having a waist opening, wherein the body portion and the crotch portion together form first and second leg openings, and the body portion is one or both of elastic or stretchable so as to provide a snug fit about the wearer's lower body part.

15. In combination:
(i) a washable, reusable garment for retention of body fluids when worn on a person's lower body part, the garment comprising: (a) a crotch portion having a washable absorbent composite incorporated in the crotch portion as part of the crotch portion by attachment thereto, and having a pocket, and (b) a body portion having a waist opening, the body portion and the crotch portion together forming first and second leg openings; and
(ii) at least one absorbent pad for insertion into the pocket.

16. The combination of claim 15, wherein the garment comprises a material chosen from woven, non-woven, or a combination thereof.

17. The combination of claim 16, wherein the material is chosen from cotton, nylon, polyester, or a combination thereof.

18. The combination of claim 16, wherein the material includes a moisture wicking agent.

19. The combination of claim 15, wherein the washable absorbent composite is incorporated in the pocket.

20. The combination of claim 19, wherein the washable absorbent composite comprises a material chosen from woven, non-woven, or a combination thereof.

21. The combination of claim 20, wherein the washable absorbent composite comprises a non-woven polyester/rayon blend.

22. The combination of claim 19, wherein the washable absorbent composite contains an antimicrobial agent.

23. The combination of claim 22, wherein the antimicrobial agent comprises silver ion.

24. The combination of claim 19, wherein the washable absorbent composite includes a barrier film.

25. The combination of claim 24, wherein the barrier film comprises polyurethane.

26. The combination of claim 24, wherein the barrier film is laminated to the washable absorbent composite.

27. The combination of claim 15, wherein the crotch portion includes on its outside a barrier film.

28. The combination of claim 15, wherein the body portion is one or both of elastic or stretchable so as to provide a snug fit about the wearer's lower body part.

29. In combination:
(i) a washable, reusable garment for retention of body fluids when worn on a person's lower body part, the garment comprising: (a) a crotch portion having a pocket, wherein the pocket has a closed end and has an open end, (b) a washable absorbent composite incorporated on one side thereof in the pocket as part of the pocket by attachment to the pocket, and having a barrier film disposed on another side thereof, inside the space defined by the pocket, and (c) a body portion having a waist opening, wherein the body portion and the crotch portion together form first and second leg openings, and the body portion is one or both of elastic or stretchable so as to provide a snug fit about the wearer's lower body part; and
(ii) at least one absorbent pad for insertion into the pocket.

30. A washable, reusable garment for retention of body fluids when worn on a person's lower body part, the garment comprising:
(a) a crotch portion adapted to be proximate to the person's crotch and having a first end and a second end;
(b) a body portion attached to the first end and second end of the crotch portion and defining a waist opening, the body portion and the crotch portion together forming first and second leg openings having first and second edges; and
(c) a washable absorbent composite attached to the crotch portion proximate to and along the first and second edges of the first and second leg openings,
wherein the washable absorbent composite and the crotch portion form a pocket.

31. The garment of claim 30, wherein the washable absorbent composite and the crotch portion define an opening proximate to at least one end of the crotch portion.

32. The garment of claim 30, wherein the crotch portion has a length extending between the first end and the second end, and a width extending substantially perpendicular to the length, and wherein the washable absorbent composite is attached to the crotch portion substantially along the width of the crotch portion proximate to one end of the crotch portion.

33. A washable, reusable garment for retention of body fluids when worn on a person's lower body part, the garment comprising:

(a) a crotch portion adapted to be proximate to the person's crotch and having a first end and a second end;

(b) a body portion attached to the first end and second end of the crotch portion and defining a waist opening, the body portion and the crotch portion together forming first and second leg openings having first and second edges; and (c) a washable absorbent composite attached to the crotch portion proximate to and along the first and second edges of the first and second leg openings, wherein the first end of the crotch portion is adapted to be proximate to the front side of the person's body and the second end of the crotch portion is adapted to be proximate to the back side of the person's body, and wherein the washable absorbent composite is attached to the crotch portion at second end of the crotch portion, such that the washable absorbent composite and the crotch portion form a pocket.

34. The garment according to claim 33, wherein the pocket is adapted for receiving a removable absorbent pad.

* * * * *